(12) United States Patent
Guthrie et al.

(10) Patent No.: US 6,239,114 B1
(45) Date of Patent: May 29, 2001

(54) COMPOSITIONS AND METHODS FOR TREATMENT OF NEOPLASTIC DISEASES WITH COMBINATIONS OF LIMONOIDS, FLAVONOIDS AND TOCOTRIENOLS

(75) Inventors: Najla Guthrie; Elzbieta Maria Kurowska, both of London (CA)

(73) Assignee: KGK Synergize, London (CA)

( * ) Notice: Subject to any disclaimer, the term of this patent is extended or adjusted under 35 U.S.C. 154(b) by 0 days.

(21) Appl. No.: 09/481,963

(22) Filed: Jan. 12, 2000

Related U.S. Application Data

(63) Continuation-in-part of application No. 08/938,640, filed on Sep. 26, 1997, now abandoned.

(51) Int. Cl.⁷ ................................................ A61K 31/70
(52) U.S. Cl. ........................... 514/32; 514/453; 514/455; 514/458
(58) Field of Search .......................... 514/35, 455, 453, 514/458

(56) References Cited

U.S. PATENT DOCUMENTS

| | | | |
|---|---|---|---|
| 3,993,793 | 11/1976 | Finney | 426/565 |
| 4,368,213 | 1/1983 | Hollenbach et al. | 426/590 |
| 4,603,142 | 7/1986 | Burger et al. | 514/456 |
| 5,041,425 | * 8/1991 | Hasegawa et al. | 514/32 |
| 5,336,685 | * 8/1994 | Prochaska et al. | 514/455 |
| 5,348,974 | 9/1994 | Wright et al. | 514/456 |
| 5,545,398 | * 8/1996 | Perricone | 424/59 |
| 5,616,355 | 4/1997 | Haast et al. | 426/384 |
| 5,808,137 | * 9/1998 | Bombardelli et al. | 560/255 |
| 5,912,265 | * 6/1999 | Bombardelli et al. | 514/452 |
| 5,919,818 | * 7/1999 | Lane et al. | 514/458 |
| 5,952,373 | * 9/1999 | Lanzendorfer et al. | 514/456 |
| 5,955,269 | * 9/1999 | Ghai et al. | 435/6 |
| 6,133,312 | * 10/2000 | Elson | 514/458 |
| 6,143,770 | * 11/2000 | Lane et al. | 514/332 |

FOREIGN PATENT DOCUMENTS

| | | |
|---|---|---|
| 5054883 | 4/1980 | (JP) . |
| 7135922 | 5/1995 | (JP) . |
| 8283154 | 10/1996 | (JP) . |
| WO98/38993 | 9/1998 | (WO) . |

OTHER PUBLICATIONS

Miller et al, Nutr. Cancer, vol. 17, #1, pp. 1–7 (abstract, Jan. 1992.*
Miller et al, Carcinogenesis, vol. 10, #8, pp. 1535–1537 (abstract, Aug. 1989.*
Lam et al, Nutr. Cancer, vol. 12, #1, pp. 43–47 (abstract), Jan. 1989.*
Kawaii et al, Biosci. Biotechnol. Biochem., vol. 63, #5, pp. 898–899 (abstract), May 1999.*
Calomme et al, Planta Med., vol. 62, #3, pp. 222–6 (abstract), Jun. 1996.*
Hirano et al. Br. J. Cancer, vol. 72, #6, pp. 1380–3 (abstract), Dec. 1995.*
Kandaswami et al, Cancer Lett., vol. 56, #2, pp. 147–52 (abstract) Feb. 1991.*
Mak et al, Life Sci., vol. 58, #15, pp. 1269–76 (abstract), 1996.*
Bracke et al, J. Natl. Cancer Inst., vol. 91, pp. 345–9, 1999.*
Carroll et al. FASEB J. vol. 9 (4), p. A868, Meeting abstract, 1995.
Formica et al. Food Chem. Toxicol. vol. 33 (12), pp. 1061–1080, abstract enclosed, 1995.
Choi et al. J. Nat. Prod.—Lloydia. vol 54 (1), pp. 218–224, abstract enclosed, 1991.
Lam, et al., 1994, Food Technology, 48:104–108.
Hasegawa, S. Et al., 1994, in Food Phyochemicals for Cancer Prevention I, eds M–t. Huang et al., American Chemical Society, 198–207.
Shin Hasegawa and Masaki Miyake, "Biochemistry and Biological Functions of Citrus Limonoids", Food Rev. Int., 12(4), 413–435 (1996).
Hertog, M.G. et al., 1993, Lancet: 342, 1007–1011.
Kurowska, E.M. et al., 1990, J. Nutr. 120:831–836.
Guthrie N. et al., 1996, Proc. Am. Inst. Cancer Res., Abs. #8.
Cummings, F.J. et al, 1985, Ann. Intern. Med. 103;324.
Boring, C.C. et al., 1993, CA Cancer J. Clin. 43:7.
Sattin, R. W. et al., 1985, JAMA 253 : 1908.
Schatzkin A. et al., 1987, N. Engl. J. Med. 316 : 1169.
Carroll, K.K., 1980, J. Env. Pathol. Tox. 3: 253–271.
Castelli, W.P. et al., 1986, JAMA 256 : 2835.
Report of the National Education Program Expert Panel on Detection, Evaluation, and Treatment of High Blood Cholesterol in Adults, 1988, Arch. Intern. Med. 148 : 36.
Monforte et al. IL FARMACO 50:595–599, 1995.
Guthrie et al. Proc Am Assoc Cancer Res 37:Abstract #1907,1996.
Bracke et al. Food Technol. 48:121–124, 1994.
Miller et al. Food Technol. 48: 112–115, 1994.

* cited by examiner

*Primary Examiner*—James H. Reamer
(74) *Attorney, Agent, or Firm*—Davidson, Davidson & Kappel, LLC

(57) ABSTRACT

Compositions and methods for the prevention and treatment of neoplastic diseases are described. Individuals at a high risk of developing or having neoplasia undergoing conventional therapies may be treated with an effective dose of triterpene derivatives in limonoids, polyphenolic flavonoid compounds, tocotrienols or a combination of these agents.

36 Claims, No Drawings

COMPOSITIONS AND METHODS FOR TREATMENT OF NEOPLASTIC DISEASES WITH COMBINATIONS OF LIMONOIDS, FLAVONOIDS AND TOCOTRIENOLS

1. CROSS REFERENCE TO RELATED APPLICATIONS

This application is a Continuation-In-Part of the U.S. patent application Ser. No. 08/938,640, filed Sep. 26, 1997 now abandoned the entire disclosure of which is incorporated by reference.

2. BACKGROUND OF THE INVENTION

The present invention relates to compositions and methods for the prevention and treatment of neoplastic and oncogenic disorders, with combinations of certain limonoids, flavonoids and/or tocotrienols. Limonoids are a group of chemically related triterpene derivatives found in the Rutaceae and Meliaceae families. Limonoids are among the bitter principals in citrus juices such as lemon, lime, orange and grapefruit. Flavonoids are polyphenolic compounds that occur unbiquitously in plant foods especially in orange, grapefruit and tangerine. Tocotrienols are present in palm oil and are a form of vitamin E having an unsaturated side chain. In the practice of the cancer prevention and/or treatment of the invention the limonoids, flavonoids and tocotrienols are used to inhibit the development progression and proliferation of cancer cells. Preferred compositions of the invention are those which specifically or preferentially prevent transformation of preneoplastic cells to tumor cells, and prevent or inhibit tumor cell proliferation, invasion and metastasis without general cytotoxic effects.

2.1 Limonoids

Limonoids are a group of chemically related triterpene derivatives found in the Rutaceae and Meliaceae families. Limonoids are among the bitter principles found in citrus fruits such as lemons, lime, orange and grapefruit. They are also present as glucose derivatives in mature fruit tissues and seed, and are one of the major secondary metabolites present in Citrus. Limonoids have been found to have anti-carcinogenic activity in laboratory animals. The furan moiety attach to the D-ring is specifically responsible for detoxifying of the chemical carcinogen glutathione-S-transferase enzyme system (Lam, et al., 1994, Food Technology 48:104–108).

Citrus fruit tissues and byproducts of juice processing such as peels and molasses are sources of limonoid glucosides and citrus seed contain high concentrations of both limonoid aglycones and glucosides. Limonoid aglycones m the fruit tissues gradually disappear during the late stages of fruit growth and maturation.

Thirty-eight limonoid aglycones have been isolated from Citrus. The limonoids are present in three different forms: the dilactone (I) is present as the open D-ring form (monolactone), the limonoate A-ring lactone (II) and the glucoside form (III). Only the monolactones and glucosides are present in fruit tissues. (Hasegawa S. et al., 1994, in Food Phytochemicals for Cancer Prevention I, eds M-T. Huang et al, American Chemical Society, 198–207).

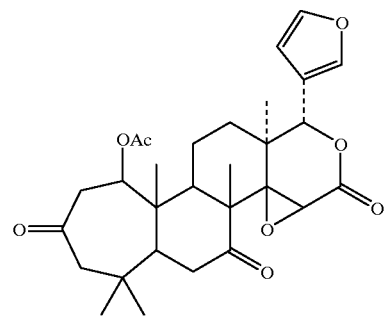

Nomillin

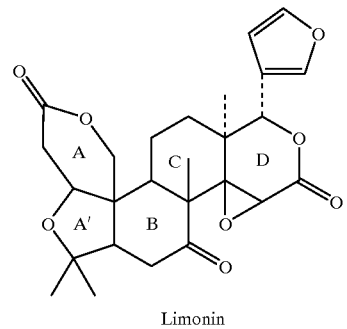

Limonin

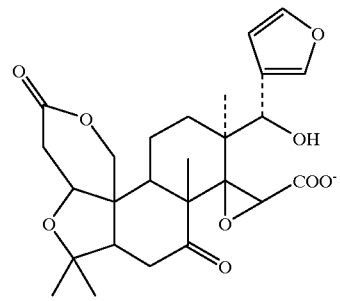

Limonoate A-ring lactone

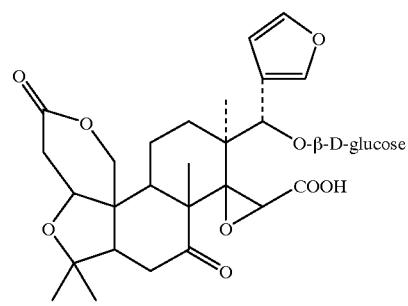

Limonin 17-β-D-glucopyranoside

Compound III is the predominant limonoid glucoside found in all juice samples. In orange juice it comprises 56% of the total limonoid glucosides present, while in grapefruit and lemon juices, it comprises an average of 63% to 66% respectively. Procedures for the extraction and isolation of both aglycones and glucosides have been established to obtain concentrated sources of various limonoids (Lam, L. K. T. et al., 1994, in Food Phytochemicals for Cancer Prevention, eds. M. Huang, T. Osawa, C. Ho and R. T.

Rosen, ACS Symposium Series 546, p 209). The use of limonoids in combination with a flavonoid, tocotrienol, a cancer chemotherapeutic agent, or a combination of any one of these agents, has not been reported for the prevention and treatment of neoplastic diseases.

2.2 Flavonoids.

Epidemiological studies have shown that flavonoids present in the Mediterranean diet may reduce the risk of death from coronary heart disease (Hertog, M. G. et al., 1993, Lancet: 342, 1007–1011). Soybean isoflavones for example, genistein, which is a minor component of soy protein preparations may have cholesterol-lowering effects (Kurowska, E. M. et al., 1990, J. Nutr. 120:831–836). The flavonoids present in citrus juices such as orange and grapefruit include, but are not limited to, hesperetin and naringenin respectively.

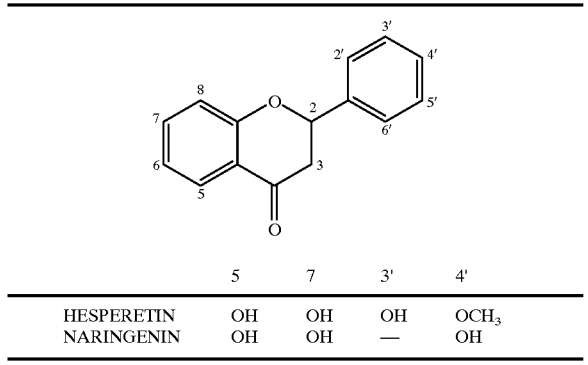

| | 5 | 7 | 3' | 4' |
|---|---|---|---|---|
| HESPERETIN | OH | OH | OH | $OCH_3$ |
| NARINGENIN | OH | OH | — | OH |

The flavonoids preset in tangerine include, but are not limited to tangerevtin or nobiletin. These flavonoids were found to inhibit growth of both estrogen receptor-negative (ER−) and positive (ER+) breast cancer cells in culture and act synergistically with tamoxifen and tocotrienols (Guthrie N. et aL, 1996, Proc. Am. Inst. Cancer Res., Abs.#8).

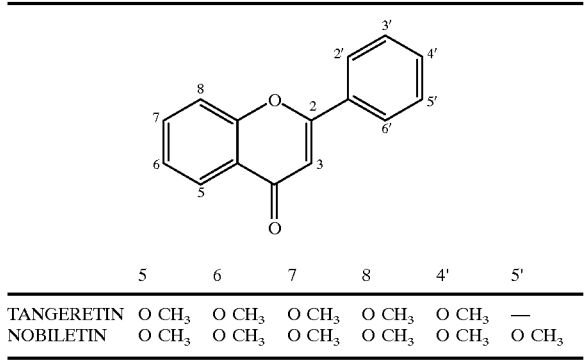

| | 5 | 6 | 7 | 8 | 4' | 5' |
|---|---|---|---|---|---|---|
| TANGERETIN | $O CH_3$ | $O CH_3$ | $O CH_3$ | $O CH_3$ | $O CH_3$ | — |
| NOBILETIN | $O CH_3$ | $O CH_3$ | $O CH_3$ | $O CH_3$ | $O CH_3$ | $O CH_3$ |

2.3 Tocotrienols in Palm Oil

Tocotrienols are present in palm oil and are a form of vitamin E having an unsaturated side chain. They include, but are not limited to alpha-tocotrienol, gamma-tocotrienol or delta-tocotrienol.

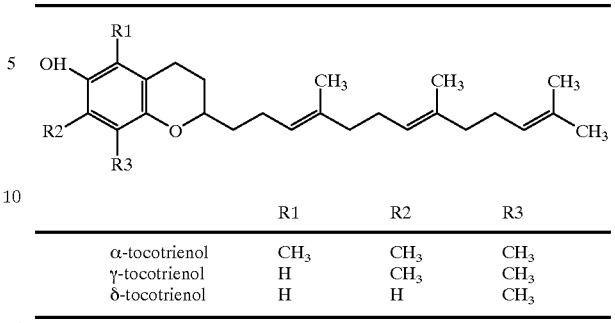

| | R1 | R2 | R3 |
|---|---|---|---|
| α-tocotrienol | $CH_3$ | $CH_3$ | $CH_3$ |
| γ-tocotrienol | H | $CH_3$ | $CH_3$ |
| δ-tocotrienol | H | H | $CH_3$ |

2.4 Cancer Growth and Chemotherapy

Cancer is a disease of inappropriate tissue accumulation. Chemotherapeutic agents share one characteristic: they are usually more effective in killing or damaging malignant cells than normal cells. However, the fact that they do harm normal cells indicates their potential for toxicity. Animal tumor investigations and human clinical trials have shown that drug combinations produce higher rates of objective response and longer survival than single agents. Combination drug therapy is, therefore, the basis for most chemotherapy employed at present (DeVita, V. T. et. al., 1995, Cancer 35:98).

Cancer treatment requires inhibitions of a variety of factors including tumor cell proliferation, metastatic dissemination of cancer cells to other parts of the body, invasion, tumor-induced neovascularization, and enhancement of host immunological responses and cytotoxicity. Conventional cancer chemotherapeutic agents have often been selected on the basis of their cytotoxicity to tumor cells. However, some anticancer agents have adverse effects on the patient's immune system. Thus it would be greatly advantageous if a cancer therapy or treatment could be developed that would afford non-cytotoxic protection against factors that might lead to progression of tumors.

Because hormone therapy as well as chemotherapy is effective in controlling advanced breast cancer, it has been used as an adjuvant to mastectomy in primary breast cancer. Patients with ER+ or ER− tumors benefit from adjuvant chemotherapy. However, tamoxifen used alone as an adjuvant to mastectomy for breast cancer shows benefit in extending disease-free and overall survival (Cummings, F. J. et al., 1985, Ann. Intern. Med. 103;324).

3. SUMMARY OF THE INVENTION

The present invention is directed to compositions and methods for the prevention and/or treatment of neoplastic diseases, which involves using a combination composition of limonoids, flavonoids and/or tocotrienols to treat an individual at high risk for, or suffering from cancer.

The present invention is also directed to compositions and methods for the prevention and/or treatment of different types of cancer, which involves using a combination composition of limonoids and flavonoids to an individual at high risk or suffering from such cancer.

The present invention is also directed to compositions and method for the prevention and/or treatment of cancer, which involves using a combination composition of flavonoids and tocotrienols to an individual at high risk or suffering from cancer.

The present invention is also directed to compositions and methods for the prevention and/or treatment of cancer, which involves using a composition of limonoids, citrus flavonoids, tocotrienols or a chemotherapeutic agent to an individual at high risk or suffering from cancer.

The present invention is directed to compositions and methods for the prevention and for treatment of neoplastic diseases, which involves using an effective dose of a combination of limonoids, flavonoids, and/or tocotrienols with or without conventional chemotherapy or hormonal and/or radiation therapy or surgery, to treat a patient suffering from cancer.

The present invention is also directed to compositions and methods for preventing immune suppression and toxicity induced by anticancer chemotherapeutic agents, using an effective dose of limonoids alone or in combination with flavonoids, to treat a patient suffering from cancer.

4. DETAILED DESCRIPTION OF THE INVENTION

The compositions and methods of the invention involve administering an effective dose of a limonoid alone or in combination with flavonoids and tocotrienols, an anticancer drug, a chemotherapeutic agent, or a specific combination of these agents, to an individual who is identified as being at enhanced risk for cancer and/or as having cancer, in order to prevent and/or treat cancer.

It may be that the ability of limonoids in combination with flavonoids or tocotrienols, to inhibit tumor cell proliferation, to inhibit the metastatic spread of tumor cells or to prevent immuno-suppression and toxicity induced by chemotherapeutic agents, contributes to their effectiveness in the prevention and treatment of neoplastic diseases. These possible mechanisms action are in no way meant to limit the scope of the invention and are presented purely for explanatory and/or illustrative purposes.

4.1 Cancer

Cancer is the second leading cause of death in the United States, after heart disease (Boring, C. C. et al., 1993, CA Cancer J. Chin. 43:7), and develops in one in three Americans, and one of every four Americans dies of cancer. Cancer can be viewed as a breakdown in the communication between tumor cells and their environment, including their normal neighboring cells. Signals, both growth-stimulatory and growth-inhibitory, are routinely exchanged between cells within a tissue. Normally, cells do not divide in the absence of stimulatory signals, and likewise, will cease dividing in the presence of inhibitory signals. In a cancerous, or neoplastic state, a cell acquires the ability to "override" these signals and to proliferate under conditions in which normal cells would not grow.

In addition to unhindered cell proliferation, cells must acquire several traits for tumor growth to occur. For example, early on in tumor development, cells must evade the host immune system. Further, as tumor mass increases, the tumor must acquire vasculature to supply nourishment and remove metabolic waste. Additionally, cells must acquire an ability to invade adjacent tissue, and ultimately cells often acquire the capacity to metastasize to distant sites.

Cancer of the breast is the most common form of malignant disease occurring among women of the Western World, and it is the most common cause of death among those who are between 40 and 45 years of age.

In North American women, characteristics that are associated with a threefold to fourfold increase in risk for breast cancer include (I) first-degree female family members (mothers and sisters) who had breast cancer, (2) prior breast cancer, (3) nulliparity, (4) age greater than 30 years at first pregnancy and (5) early menarche or late menopause (Sattin, R. W. et al, 1985, JAMA 253:1908). International studies have demonstrated a positive correlation between per capita consumption of fat and alcohol (Schatzkin A. et al., 1987, N. Engl. J. Med. 316: 1169) and the incidence of breast cancer. (Carroll K. K., 1980, J. Env.Pathol. Tox. 3: 253–271). Several studies have linked the consumption of fresh fruits and vegetables, and vitamin E with reduced risk of developing cancer, including breast cancer (Steinmetz, K. A. et al., 1991, Cancer Causes Control 2 : 427–442). Although this protective effect has been generally attributed to the antioxidant capacities of vitamin C and beta-carotene present in these foods, it may be related to other phytochemical constituents such as citrus limonoids and flavonoids. The use of limonoids, flavonoids or tocotrienols alone or in combination with each other or with a cancer chemo-therapeutic agent has not been reported for the prevention and treatment of neoplastic diseases.

The present invention provides a number of different limonoids comprising, but not limited to, limonin, nomilin, limonin glucoside or glucoside mixture, flavonoids comprising nobiletin or tangeretin and tocotrienol comprising alpha-tocotrienol, gamma-tocotrienol or delta-tocotrienol.

Cancers that can be prevented and/or treated by the compositions and methods of the present invention include, but are not limited to, human sarcomas and carcinomas, e.g. carcinomas, e.g., colon carcinoma, pancreatic cancer, breast cancer, ovarian cancer, prostate cancer, fibrosarcoma, myxosarcoma, liposarcoma, chondrosarcoma, osteogenic sarcoma, chondroma, angiosarcoma, endotheliosarcoma, lymphangiosarcoma, lymphangioendotheliosarcoma, synovioma, mesothelioma, Ewing's tumor, leiomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wiims' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, and heavy chain disease. Specific examples of such cancers are described in the sections below.

Advances in the study of the role of antioxidants in the maintenance of life-from cellular to the most complex organisms-has been recognized. Flavonoids consist of at least two phenyl rings separated by a pyran ring. The antioxidant activity of flavonoids critically depends on the part of the polyphenol molecule with better electron-donating properties. The ability of flavonoids to annihilate superoxide, and alkyl peroxy radicals is particularly important. These peroxy radicals are sufficiently unreactive in biological media to escape inconsequential reactions at the site of generation, yet they are precursors of considerably more reactive and damaging hydroxyl and alkoxyl radicals. Quenching of singlet oxygen by flavonoids is very fast and efficient and flavonoids may be involved in the restitution of vitamin E. The use of flavonoids alone or in combination with limonoids, tocotrienols or vitamin E in living organisms offers a promising and beneficial role in prevention and therapy of cancer.

4.2 Dosage and Formulations

Limonoids, flavonoids or tocotrienols may be formulated into pharmaceutical preparations for administration to mammals for prevention and treatment of neoplastic and oncogenic diseases.

Many of the limonoids, flavonoids or tocotrienols may be provided as compounds with pharmaceutically compatible counterions, a form in which they may be soluble.

The therapeutic compounds or pharmaceutical compositions may be administered intravenously, intraperitoneally, subcutaneously, intramuscularly, intrathecally, orally, rectally, topically or by aerosol.

Formulations suitable for oral administration include liquid solutions of the active compound dissolved in diluents such as saline, water or PEG 400; capsules or tablets, each containing a predetermined amount of the active agent as solid, granules or gelatin; suspensions in an approximate medium; and emulsions.

Formulations suitable for parenteral administration include aqueous and non-aqueous isotonic sterile solutions, which contain buffers, antioxidants and preservatives. The formulations may be in unit dose or multi-dose sealed containers.

Formulations suitable for topical administration include creams which contain limonoids, flavonoids and/or tocotrienols in various suitable combinations alone or in combination with a chemotherapeutic agent.

Patient dosages for oral administration of limonoids range from 1–500 mg/day, commonly 1–100 mg/day, and typically from 1–100 mg/day. Stated in terms of patient body weight, usual dosages range from 0.01–10 mg/kg/day, commonly from 0.01–2.0 mg/kg/day, typically from 0.01 to 2.0 mg/kg/day.

Patient dosages for oral administration of flavonoids range from 200–5000 mg/day, commonly 1000–2000 mg/day, and typically from 500–1500 mg/day. Stated in terms of patient body weight, usual dosages range from 15–70 mg/kg/day, commonly from 15–30 mg/kg/day, typically from 7–21 mg/kg/day.

Patient dosages for oral administration of tocotrienols range from 1–1200 mg/day, commonly 1–100 mg/day, and typically from 1–60 mg/day. Stated in terms of patient body weight, usual dosages range from 0.01–20 mg/kg/day, commonly from 0.01–2.0 mg/kg/day, typically from 0.01 to 1.0 mg/kg/day.

Dosage amount and interval may be adjusted individually to provide plasma levels of the active moiety which are sufficient to maintain the anti-proliferative and anti-metastatic effects.

Alternatively, one may administer the compound in a local, rather than oral manner, for example, via injection of the compound directly into a tumor, often in a depot or sustained release formulation.

A variety of delivery systems for the pharmacological compounds may be employed, including, but not limited to, liposomes and emulsions. The pharmaceutical compositions also may comprise suitable solid or gel phase carriers or excipients. Examples of such carriers or excipients include, but are not limited to, calcium carbonate, calcium phosphate, various sugars, starches, cellulose derivatives, gelatin, and polymers such as polyethylene glycols.

Furthermore, one may administer the agent in a targeted drug delivery system, for example, in a liposome coated with tumor-specific antibody. The liposomes will be targeted to and taken up selectively by the tumor.

In cases of local administration or selective uptake, the effective local concentration of the drug may not be related to plasma concentration.

5. EXAMPLE

Effects of Limonoids, Flavonoids, Tocotrienols and Combinations of each in Four different tumor cell lines (a) The effect of nomilin, limonin, naringenin, hesperitin, nobiletin, tangeretin, alpha-tocotrienol, delta-tocotrienol and gamma-tocotrienol on the proliferation and growth of human prostatic tumor DU 145 cells, human colon cancer HT29 cells, the DMS 114 human lung cancer cells and the human SK-MEL-5 melanoma cells was studied in vitro, as measured by the incorporation of [$^3$H] Thymidine.

Materials: Tissue culture medium and fetal calf serum were purchased from Gibco, Burlington, ON. Thymidine was purchased from ICN, Irvine, Calif.

TRF and the individual tocotrienols were obtained from the Palm Oil Research Institute of Malaysia (PORIM), Kuala Lumpur. Hesperetin, nobiletin and tangeretin were obtained from State of Florida, Department of Citrus Lake Alfred, FL. Apigenin, genistein, hesperetin, and naringenin were purchased from the Sigma Chemical Co., St. Louis, Mo.

Cell Culture: Each of the four human tumor cell lines were maintained at 37° C. in a minimum essential medium, supplemented with 10% (v/v) fetal bovine serum. The medium was equilibrated with a humidified atmosphere of 5% $CO_2$. Stock cultures were seeded at a density of $2 \times 10^5$ cells/ml and allowed to multiply for 48 to 72 hours.

Incorporation of [3H] Thymidine Into DNA: Each of the four human tumor cell lines were plated at $5 \times 10^3$ to $4 \times 10^4$ cells/well (depending on the doubling time of each individual cell line) in 96-well, flat bottomed, culture plates in a total volume of 200 $\mu$L of medium and incubated at 37° C. for 48 hours with or without test compounds. [$^3$H] Thymidine (0.5 $\mu$Ci/well) was then added and after 4 hours. The cells were removed by trypsinization at specified times and counted using a hemocytometer. The cells were harvested onto a glass fibre filter paper using a semiautomatic 12-well cell harvester (Skatron Inc., Sterling, Va). Radioactivity on the filter paper was counted using Scinteverse in a liquid scintillation counter. The % of dividing cells was determined as an average of 3 wells for each concentration tested and expressed as a function of the average of the control. For each cell line the concentration at which 50% growth inhibition occurred using each test agent or combination was determined to represent the IC 50 in microgram per ml. Table 1 represents the overall results obtained using the following combinations: limonin, nomilin, naringenin, hesperetin, nobiletin, tangeretin, alpha-tocotrienol, delta-tocotrienol, garmma-tocotrienol,limonin+naringenin, limonin+tangeretin, nomilin+tangeretin, limorin+ tangeretin+alpha-tocotrienol, limonin+nobiletin+alpha tocotrienol,nomilin+naringenin+alpha tocotrienol, and nomilin+hesperetin+alpha-tocotrienol.

Results—The test compounds alone or in combination, had important effects on the proliferation of the four human tumor cell lines in vitro. See Table 1.

In the DU145 prostatic tumor cell line, tangeretin alone or nobiletin alone inhibited these cells most effectively followed by nomilin when the test agents were given alone. When given as combinations, the most effective combination was nomilin+hesperitin+alpha tocotrienol, followed by limolin+nobelitin+alpha-tocotrienol and nomilin+naringenin, followed by nomilin+hesperitin+alpha tocotrienol and limonin+tangeretin+alpha-tocopherol, followed by nomilin+tangeretin and limonin+tangeretin, followed by limonin+naringenin.

In the HT29 colon tumor cells, starting with the most active antiproliferative agent, the results were, nomilin+tangeretin, limonin+naringenin, tangeretin, limonin+tangeretin+alpha-tocotrienol, nobiletin, nomilin+hesperetin+alpha-tocotrienol, nomilin+tangeretin, nomilin+naringenin+alpha=tocotrienol, limonin+tangeretin, limonin+nobiletin+alpha-tocotrienol, gamma-tocotrienol, limonin, naringenin, hesperitin and delta-tocotrienol.

In the DMS 114 lung tumor cells, starting with the most active antiproliferative agent the results were tangeretin, nobiletin, nomilim+naringenin+alpha-tocotrienol, nomilin+tangeretin, limonin+tangeretin, limonin+nobiletin+alha-tocotrienol, nomilin+hesperitin+alpha-tocotrienol, nomilin, limonin, naringenin, hesperitin, delta-tocotrienol and alpha-tocotrienol.

In the SK-MEK 5 melanoma cells, starting with the most active antiproliferative activity, the results were nomilin+tangeretin, limolin+tangeretin+alpha-tocopherol, limonin+nobiletin+alpha-tocotrienol, limonin+tangeretin, nobiletin, tangeretin, nomilin+naringenin+alpha-tocotrienol, nomilin+hesperitin+alpha-tocotrienol, gamma-tocotrienol, nomilin, limonin, delta-tocotrienol, limonin+naringenin, and naringenin, hesperitin, or nomilin+naringenin.

TABLE 1

| Compound | DU145 (prostate) | HT29 (colon) | DMS 114 (Lung) | SK-MEL-5 (Melanoma) |
|---|---|---|---|---|
| Limonin | 75 | 60 | 70 | 125 |
| nomilin | 40 | 25 | 35 | 95 |
| Naringenin | 95 | 75 | 75 | 200 |
| Hesperetin | 125 | 95 | 85 | 200 |
| Nobiletin | 10 | 7 | 9 | 25 |
| Tangeretin | 10 | 5 | 5 | 32 |
| α-T3 | 125 | 95 | 95 | 200 |
| δ-T3 | 90 | 75 | 90 | 125 |
| γ-T3 | 75 | 55 | 75 | 95 |
| Limonin + naringenin | 100 | 0.1* | 200 | 100 |
| Limonin + tangeretin | 50 | 25 | 25 | 22 |
| Nomilin + naringenin | 20* | 0.02* | 200 | 200 |
| Nomilin + tangeretin | 40 | 22 | 30 | 4* |
| Limonin + tangeretin + α-T3 | 33 | 6 | 33 | 6* |
| Limonin + nobiletin + α-T3 | 20 | 30 | 35 | 6* |
| Nomilin + naringenin + α-T3 | 10* | 25* | 10* | 35* |
| Nomilin + hesperetin + α-T3 | 35* | 20* | 35* | 40* |

*Synergistic Combinations IC 50 microgram/ml

Nobiletin alone or tangeretin alone had significant antiproliferative effect in all the four tumor cell lines. In the combinations, nomilin+naringenin+alpha-tocotrienol and nomilin+hesperitin+alpha-tocotrienol had significant anticancer effects in all tumor cell lines. These results indicate that the flavonoids nobiletin or tangeretin have anticancer effects when given alone. In addition, the combination of different flavonoids, limonoids and alpha-tocotrienol demonstrated significant anti-cancer effects in four different tumor cell lines, indicating a potential anticancer effect in general.

The present invention is not to be limited in scope by the embodiments disclosed in the examples which are intended as an illustration of one aspect of the invention and any methods which are functionally equivalent are within the scope of the invention. Indeed, various modifications of the invention in addition to those shown and described herein will become apparent to those skilled in the art from the foregoing description. Such modifications are intended to fall within the scope of the appended claims.

Various publications are cited herein, the disclosures of which are incorporated by reference in their entireties.

What is claimed is:

1. A pharmaceutical composition comprising a synergistic combination of at least two compounds selected from the group consisting of a limonoid, a flavonoid and a tocotrienol for treating a mammal at risk of or suffering from cancer, said composition exhibiting synergistic anti-proliferative activity against at least one form of cancer.

2. The pharmaceutical composition according to claim 1, wherein said limonoid is selected from the group consisting of limonin and nomilin, said flavonoid is selected from the group consisting of naringenin, hesperetin, nobiletin and tangeretin, and said tocotrienol is selected from the group consisting of alpha-tocotrienol, gamma-tocotrienol and delta-tocotrienol.

3. The pharmaceutical composition according to claim 1, wherein said composition is suitable for administration intravenously, intraperitoneally, subcutaneously, intramuscularly, intrathecally, orally, rectally, topically or by inhalation.

4. The pharmaceutical composition according to claim 3, wherein said composition is suitable for administration intravenously.

5. The pharmaceutical composition according to claim 3, wherein said composition is suitable for administration orally.

6. The pharmaceutical composition according to claim 1, wherein said composition is in the form of a tablet, a capsule, a solution, a suspension, or an emulsion.

7. The pharmaceutical composition according to claim 1, further comprising an anti-neoplastic amount of a chemotherapeutic agent.

8. The pharmaceutical composition according to claim 1, wherein said limonoid is nomilin and said flavonoid is selected from the group consisting of naringenin and tangeretin.

9. The pharmaceutical composition according to claim 2, wherein said synergistic combination comprises limonin and naringenin and said composition exhibits anti-proliferative activity against HT-29 colon tumor cells.

10. The pharmaceutical composition according to claim 2, wherein said synergistic combination comprises nomilin and naringenin and said composition exhibits anti-proliferative activity against DU 145 prostate tumor cells and HT-29 colon tumor cells.

11. The pharmaceutical composition according to claim 2, wherein said synergistic combination comprises nomilin and tangeretin and said composition exhibits anti-proliferative activity against SK-MEL-5 melanoma tumor cells.

12. The pharmaceutical composition according to claim 1, wherein said said tocotrienol is alpha-tocotrienol.

13. The pharmaceutical composition according to claim 2, wherein said synergistic combination comprises limonin, tangeretin and alpha-tocotrienol and said composition exhibits anti-proliferative activity against SK-MEL-5 melanoma tumor cells.

14. The pharmaceutical composition according to claim 2, wherein said synergistic combination comprises limonin, nobiletin and alpha-tocotrienol and said composition exhibits anti-proliferative activity against SK-MEL-5 melanoma tumor cells.

15. The pharmaceutical composition according to claim 2, wherein said synergistic combination comprises nomilin, naringenin and alpha-tocotrienol and said composition exhibits anti-proliferative activity against DU-145 prostate tumor cells, HT-29 colon tumor cells, DMS 114 lung tumor cells and SK-MEL-5 melanoma tumor cells.

16. The pharmaceutical composition according to claim 2, wherein said synergistic combination comprises nomilin, hesperetin and alpha-tocotrienol and said composition exhibits anti-proliferative activity against DU-145 prostate tumor cells, HT-29 colon tumor cells, DMS 114 lung tumor cells and SK-MEL-5 melanoma tumor cells.

17. A method of treating an individual at risk of or suffering from cancer, comprising;
   administering to an individual a pharmaceutical composition comprising a synergistic combination of at least two compounds selected from the group consisting of a limonoid, a flavonoid and a tocotrienol, said composition exhibiting synergistic anti-proliferative activity against at least one form of cancer.

18. The method of claim 17, wherein said limonoid is selected from the group consisting of limonin and nomilin, said flavonoid is selected from the group consisting of naringenin, hesperetin, nobiletin and tangeretin, and said tocotrienol is selected from the group consisting of alpha-tocotrienol, gamma-tocotrienol and delta-tocotrienol.

19. The method of claim 17, wherein said composition is administered intravenously, intraperitoneally, subcutaneously, intramuscularly, intrathecally, orally, rectally, topically or by inhalation.

20. The method of claim 19, wherein said composition is administered intravenously.

21. The method of claim 19, wherein said composition is administered orally.

22. The method of claim 17, wherein said composition is in the form of a tablet, a capsule, a solution, a suspension, or an emulsion.

23. The method of claim 17, wherein said synergistic combination is administered in a single or divided dose and provides from about 1 mg/day to about 500 mg/day of said limonoid, from about 200 mg/day to about 5000 mg/day of said flavonoid and from about 1 mg/day to about 1200 mg/day of said tocotrieniol.

24. The method of claim 17, wherein said synergistic combination is administered in a single or divided dose and provides from about 0.01 mg/kg/day to about 10 mg/kg/day of said limonoid, from about 15 mg/kg/day to about 70 mg/kg/day of said flavonoid and from about 0.01 mg/kg/day to about 20 mg/kg/day of said tocotrienol.

25. The method of claim 17, wherein said synergistic combination is administered in a single or divided dose and provides from about 7 mg/kg/day to about 21 mg/kg/day of said flavonoid.

26. The method according to claim 17, further comprising administering an anti-neoplastic amount of a chemotherapeutic agent.

27. The method according to claim 17, wherein said limonoid is nomilin and said flavonoid is selected from the group consisting of naringenin and tangeretin.

28. The method according to claim 18, wherein said synergistic combination comprises limonin and naringenin and said composition exhibits anti-proliferative activity against HT-29 colon tumor cells.

29. The method according to claim 18, wherein said synergistic combination comprises nomolin and naringenin and said composition exhibits anti-proliferative activity against DU 145 prostate tumor cells and HT-29 colon tumor cells.

30. The method according to claim 18, wherein said synergistic combination comprises nomolin and tangeretin and said composition exhibits anti-proliferative activity against SK-MEL-5 melanoma tumor cells.

31. The method according to claim 17, wherein said tocotrienol is alpha-tocotrienol.

32. The method of claim 18, wherein said synergistic combination comprises limonin, tangeretin and alpha-tocotrienol and said composition exhibits anti-proliferative activity against SK-MEL-5 melanoma tumor cells.

33. The method according to claim 18, wherein said synergistic combination comprises limonin, nobiletin and alpha-tocotrienol and said composition exhibits anti-proliferative activity against SK-MEL-5 melanoma tumor cells.

34. The method according to claim 18, wherein said synergistic combination comprises nomolin, naringenin and alpha-tocotrienol and said composition exhibits anti-proliferative activity against DU-145 prostate tumor cells, HT-29 colon tumor cells, DMS 114 lung tumor cells and SK-MEL-5 melanoma tumor cells.

35. The method according to claim 18, wherein said synergistic combination comprises nomolin, hesperetin and alpha-tocotrienol and said composition exhibits anti-proliferative activity against DU-145 prostate tumor cells, HT-29 colon tumor cells, DMS 114 lung tumor cells and SK-MEL-5 melanoma tumor cells.

36. The method according to claims 17 wherein said cancer is selected from the group consisting of colon carcinoma, breast cancer, pancreatic cancer, ovarian cancer, prostate cancer, fibrosarcoma, myxosarcoma, liposarcoma, chondrosarcoma, osteogenic sarcoma, chordoma, angiosracoma, endotheliosarcoma, lymphangeosarcoma, lymphangeoendothelia sarcoma, synovioma, mesothelioma, Ewing's tumor, leiomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinomas, cystandeocarcinoma, medullary carcinoma, bronchogenic carcinoma, renal cell carcinoma, hepatoma, bile duct carcinoma, choriocarcinoma, seminoma, embryonal carcinoma, Wiims' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroama, oligodendroglioma, meningioma, melanoma, neuroblastoma, retinoblastoma, leukemias, e.g., acute lymphocytic leukemia and acute myelocytic polycythemia vera, lymphoma, multiple myeloma, Waldenstrom's macroglobulinemia, and heavy chain disease.

* * * * *